US006458167B1

(12) United States Patent
Genet et al.

(10) Patent No.: US 6,458,167 B1
(45) Date of Patent: Oct. 1, 2002

(54) USE OF CATIONIC PHENYL-AZO-BENZENE COMPOUNDS FOR DYEING KERATIN FIBERS, DYE COMPOSITIONS AND DYEING PROCESSES

(75) Inventors: Alain Genet, Aulnay sous Bois; Alan Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/484,998

(22) Filed: Jan. 18, 2000

(30) Foreign Application Priority Data

Jan. 19, 1999 (FR) .............................. 99 00506

(51) Int. Cl.⁷ ................................ A61K 7/13
(52) U.S. Cl. .................. 8/405; 8/407; 8/411; 8/429; 8/662; 534/630; 534/676; 534/857
(58) Field of Search .................. 8/405, 407, 411, 8/429, 662; 534/630, 676, 857

(56) References Cited

U.S. PATENT DOCUMENTS

| 5,409,502 A | * 4/1995 | Braun .......................... 8/405 |
| 5,976,195 A | * 11/1999 | de la Mettrie et al. ......... 8/411 |
| 6,010,541 A | * 1/2000 | de la Mettrie et al. ......... 8/412 |

FOREIGN PATENT DOCUMENTS

| DE | 198 02 940 | 8/1999 |
| FR | 1 221 122 | 5/1960 |
| FR | 909700 | * 10/1962 |
| FR | 1 533 643 | 11/1968 |
| FR | 1 565 247 | * 4/1969 |
| FR | 2 757 388 | 6/1998 |
| WO | WO 99/03836 | 1/1999 |

OTHER PUBLICATIONS

English language Derwent Abstract of DE 198 02 940, Aug. 1999.
Chemical Abstracts, vol. 72, No. 2, Jan. 12, 1970, Abstract No. 4329y (JP 06 910910), May 20, 1969.
English language Derwent Abstract of FR 2 757 388, Jun. 1998.

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett & Dunner, L.L.P.

(57) ABSTRACT

The invention relates to dyeing compositions containing phenyl-azo-benzene compounds comprising at least one cationic group Z, Z being chosen from quaternized aliphatic chains, aliphatic chains comprising at least one quaternized saturated ring and aliphatic chains comprising at least one quaternized unsaturated ring, to the use of such compositions as direct dyes in dyeing applications for keratin substances, in particular human keratin fibers and especially the hair, and to the direct dyeing processes employing these compositions.

20 Claims, No Drawings

USE OF CATIONIC PHENYL-AZO-BENZENE COMPOUNDS FOR DYEING KERATIN FIBERS, DYE COMPOSITIONS AND DYEING PROCESSES

The present invention relates to dyeing compositions containing phenyl-azo-benzene compounds comprising at least one cationic group Z chosen from quaternized aliphatic chains, aliphatic chains comprising at least one quaternized saturated ring and aliphatic chains comprising at least one quaternized unsaturated ring, to the use of such compositions as direct dyes in dyeing applications for keratin substances, in particular human keratin fibers and especially the hair, and to the direct dyeing processes employing these compositions.

In the field of hair dyeing, direct dyes are sought, i.e., dyes which, without an oxidizing agent being supplied, are capable by themselves of temporarily modifying the natural shade of the hair, while satisfying a certain number of criteria. In particular, it is desired that these direct dyes generate reproducible dyeing effects with rich and varied shades, making it possible to obtain a wide range of colors capable of satisfying formulators, and that these dyeing effects are intense and fast with respect to washing, rubbing, light and perspiration.

The inventors have just discovered, entirely surprisingly and unexpectedly, that phenyl-azo-benzene compounds of formula (I) defined below, comprising at least one cationic group Z chosen from quaternized aliphatic chains, aliphatic chains comprising at least one quaternized saturated ring and aliphatic chains comprising at least one quaternized unsaturated ring, are suitable for use as direct dyes for direct dyeing, and also that they make it possible to obtain dye compositions which lead to intense and varied colorations which have excellent properties of fastness with respect to the various treatments to which keratin fibers properties of fastness with respect to the various treatments to which keratin fibers may be subjected. Finally, these compounds display better solubility in the media conventionally used for dyeing keratin fibers and are found to be easy to synthesize.

These discoveries form the basis of the present invention.

A first subject of the invention is thus the use, as direct dyes, in, or for the manufacture of, dye compositions for keratin substances, and in particular for human keratin fibers such as the hair, of phenyl-azo-benzene compounds of formula (I) below, and the acid addition salts thereof:

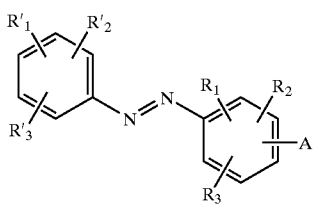

(I)

in which:

$R_1$, $R_2$, $R_3$, $R'_1$, $R'_2$ and $R'_3$, which may be identical or different, represent a hydrogen atom; a halogen atom; a group Z defined below; a ($C_1$–$C_6$)alkylcarbonyl radical; an amino($C_1$–$C_6$)alkylcarbonyl radical; an N-Z-amino($C_1$–$C_6$)alkylcarbonyl radical; an N-($C_1$–$C_6$)alkylamino($C_1$–$C_6$)alkylcarbonyl radical; an N,N-di($C_1$–$C_6$)alkylamino($C_1$–$C_6$)alkylcarbonyl radical; an amino($C_1$–$C_6$)alkylcarbonyl-($C_1$–$C_6$)alkyl radical; an N-Z-amino($C_1$–$C_6$)-alkylcarbonyl($C_1$–$C_6$)alkyl radical; an N-($C_1$–$C_6$)-alkylamino($C_1$–$C_6$)alkylcarbonyl($C_1$–$C_6$)alkyl radical; an N,N-di($C_1$–$C_6$)alkylamino($C_1$–$C_6$)alkylcarbonyl-($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N-Z-aminosulphonyl radical; a $C_1$–$C_6$ N-alkylaminosulphonyl radical; a $C_1$–$C_6$ N,N-dialkylaminosulphonyl radical; a $C_1$–$C_6$ aminosulphonylalkyl radical; a $C_1$–$C_6$ N-Z-aminosulphonylalkyl radical; an N-($C_1$–$C_6$)-alkylaminosulphonyl($C_1$–$C_6$)alkyl radical; an N,N-di($C_1$–$C_6$)alkylaminosulphonyl($C_1$–$C_6$)alkyl radical; a carbamyl radical; an N-($C_1$–$C_6$)alkylcarbamyl radical; an N,N-di($C_1$–$C_6$)alkylcarbamyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ trifluoroalkyl radical; a cyano radical; a nitro radical; an amino group $NR_4R_5$ in which $R_4$ and $R_5$ are defined below; a group $OR_6$ or $SR_6$ in which $R_6$ is defined below; or a $C_1$–$C_6$ aminoalkyl radical in which the alkyl may be unsubstituted or substituted with one or more hydroxyl radicals and in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N-($C_1$–$C_6$)alkylcarbamyl or N,N-di($C_1$–$C_6$) alkylcarbamyl, $C_1$–$C_6$ alkylsulphonyl, formyl, trifluoro ($C_1$–$C_6$)alkylcarbonyl, ($C_1$–$C_6$)alkylcarboxyl and thiocarbamyl radicals, or with a group Z defined below;

A represents a group $NR_4R_5$ in which $R_4$ and $R_5$ are defined below or a group $OR_6$ in which $R_6$ is defined below;

$R_4$ and $R_5$, which may be identical or different, represent a hydrogen atom; a group Z defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy ($C_1$–$C_6$)alkyl radical; an aryl radical; a benzyl radical; a cyano($C_1$–$C_6$)alkyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a thio-carbamyl($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$)alkyl-aminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the alkyl can be unsubstituted or substituted with one or more hydroxyl radicals radicals which are chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N-($C_1$–$C_6$)alkylcarbamyl or N,N-di($C_1$–$C_6$)-alkylcarbamyl, $C_1$–$C_6$ alkylsulphonyl, formyl, trifluoro-($C_1$–$C_6$)alkylcarbonyl, ($C_1$–$C_6$)alkylcarboxyl, thiocarbamyl radicals, and a group Z defined below, or which may together form, with the nitrogen atom to which they are attached, a carbonaceous 5- or 6-membered ring or a 5- or 6-membered ring comprising one or more identical or different hetero atoms;

$R_6$ denotes a hydrogen atom; a $C_1$–$C_6$ alkyl radical; a $C_1$–$C_6$ monohydroxyalkyl radical; a $C_2$–$C_6$ polyhydroxyalkyl radical; a group Z; a $(C_1–C_6)$alkoxy$(C_1–C_6)$ alkyl radical; an aryl radical; a benzyl radical; a carboxy$(C_1–C_6)$alkyl radical; a $(C_1–C_6)$alkylcarboxy$(C_1–C_6)$alkyl radical; a cyano$(C_1–C_6)$alkyl radical; a carbamyl$(C_1–C_6)$alkyl radical; an N-$(C_1–C_6)$alkylcarbamyl$(C_1–C_6)$alkyl radical; an N,N-di$(C_1–C_6)$alkylcarbamyl$(C_1–C_6)$alkyl radical; a $C_1–C_6$ trifluoroalkyl radical; a $C_1–C_6$ aminosulphonylalkyl radical; a $C_1–C_6$ N-Z-amino-sulphonylalkyl radical; an N-$(C_1–C_6)$alkyl-aminosulphonyl$(C_1–C_6)$alkyl radical; an N,N-di$(C_1–C_6)$alkylaminosulphonyl$(C_1–C_6)$alkyl radical; a $(C_1–C_6)$alkylsulphinyl$(C_1–C_6)$alkyl radical; a $(C_1–C_6)$-alkylsulphonyl$(C_1–C_6)$alkyl radical; a $(C_1–C_6)$-alkylcarbonyl$(C_1–C_6)$alkyl radical; a $C_1–C_6$ aminoalkyl radical in which the alkyl is unsubstituted or substituted with one or more hydroxyl radicals; a $C_1–C_6$ aminoalkyl radical in which the alkyl is unsubstituted or substituted with one or more hydroxyl radicals and in which the amine is substituted with one or two identical or different radicals which are chosen from $C_1–C_6$ alkyl, $C_1–C_6$ monohydroxyalkyl, $C_2–C_6$ polyhydroxyalkyl, $(C_1–C_6)$alkylcarbonyl, formyl, trifluoro$(C_1–C_6)$alkylcarbonyl, $(C_1–C_6)$alkylcarboxyl, carbamyl, N-$(C_1–C_6)$alkylcarbamyl, N,N-di$(C_1–C_6)$alkylcarbamyl, thiocarbamyl, $C_1–c_6$ alkylsulphonyl radicals, and a group Z defined below, or which may together form, with the nitrogen atom to which they are attached, a carbonaceous 5- or 6-membered ring or a 5- or 6-membered ring comprising one or more identical or different hetero atoms;

Z is chosen from the unsaturated cationic groups of formulae (II) and (III) below, and the saturated cationic groups of formula (IV) below:

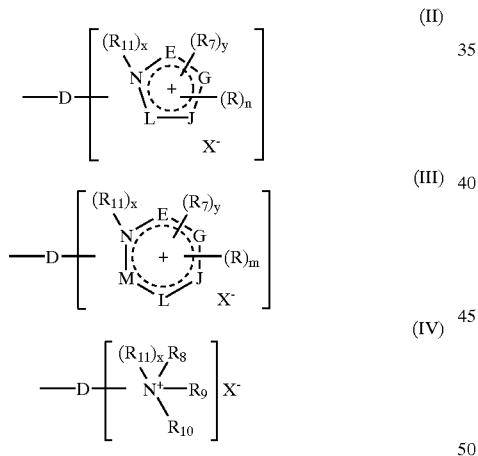

in which:

D is a linker arm which represents a linear or branched alkyl chain preferably comprising from 1 to 14 carbon atoms, which can be interrupted by one or more identical or different hetero atoms, such as oxygen, sulphur or nitrogen atoms, can be substituted with one or more hydroxyl or identical or different $C_1–C_6$ alkoxy radicals, and can bear one or more ketone functions;

the ring members E, G, J, L and M, which may be identical or different, represent a carbon, oxygen, sulphur or nitrogen atom;

n is an integer ranging from 0 to 4;

m is an integer ranging from 0 to 5;

the radicals R, which may be identical or different, represent a second group Z which is identical to or different from the first group Z; a halogen atom; a hydroxyl radical; a $C_1–C_6$ alkyl radical; a $C_1–C_6$ monohydroxyalkyl radical; a $C_2–C_6$ polyhydroxyalkyl radical; a nitro radical; a cyano radical; a cyano$(C_1–C_6)$alkyl radical; a $C_1–C_6$ alkoxy radical; a tri$(C_1–C_6)$alkylsilane$(C_1–C_6)$alkyl radical; an amido radical; an aldehydo radical; a carboxyl radical; a $(C_1–C_6)$alkylcarbonyl radical; a thio radical; a $C_1–C_6$ thioalkyl radical; a $C_1–C_6$ alkylthio radical; an amino radical; an amino radical protected with a $(C_1–C_6)$alkylcarbonyl, carbamyl or $C_1–C_6$ alkylsulphonyl radical; or a group NHR" or NR" R'" in which R" and R'", which may be identical or different, represent a $C_1–C_6$ alkyl radical, a $C_1–C_6$ monohydroxyalkyl radical or a $C_2–C_6$ polyhydroxyalkyl radical;

$R_7$ represents a $C_1–C_6$ alkyl radical; a $C_1–C_6$ monohydroxyalkyl radical; a $C_2–C_6$ polyhydroxyalkyl radical; a cyano$(C_1–C_6)$alkyl radical; a tri$(C_1–C_6)$alkylsilane$(C_1–C_6)$alkyl radical; a $(C_1–C_6)$alkoxy$(C_1–C_6)$alkyl radical; a carbamyl-$(C_1–C_6)$alkyl radical; a $(C_1–C_6)$alkylcarboxy$(C_1–C_6)$-alkyl radical; a benzyl radical; or a second group Z which is identical to or different from the first group Z;

$R_8$, $R_9$ and $R_{10}$, which may be identical or different, represent a $C_1–C_6$ alkyl radical; a $C_1–C_6$ monohydroxyalkyl radical; a $C_2–C_6$ polyhydroxyalkyl radical; a $(C_1–C_6)$alkoxy$(C_1–C_6)$alkyl radical; a cyano$(C_1–C_6)$alkyl radical; an aryl radical; a benzyl radical; a $C_1–C_6$ amidoalkyl radical; a tri$(C_1–C_6)$alkylsilane$(C_1–C_6)$alkyl radical; or a $C_1–C_6$ aminoalkyl radical in which the amine is protected with a $(C_1–C_6)$alkylcarbonyl, carbamyl or $C_1–C_6$ alkylsulphonyl radical; two of the radicals $R_8$, $R_9$ and $R_{10}$, may also form, together with the nitrogen atom to which they are attached, a carbonaceous saturated 5- or 6-membered ring or a 5- or 6-membered ring comprising one or more identical or different hetero atoms, such as, for example, a pyrrolidine ring, a piperidine ring, a piperazine ring or a morpholine ring, it being possible for the ring to be unsubstituted or substituted with a halogen atom, a hydroxyl radical, a $C_1–C_6$ alkyl radical, a $C_1–C_6$ monohydroxyalkyl radical, a $C_2–C_6$ polyhydroxyalkyl radical, a nitro radical, a cyano radical, a cyano$(C_1–C_6)$alkyl radical, a $C_1–C_6$ alkoxy radical, a tri$(C_1–C_6)$alkylsilane$(C_1–C_6)$alkyl radical, an amido radical, an aldehydo radical, a carboxyl radical, a keto$(C_1–C_6)$alkyl radical, a thio radical, a $C_1–C_6$ thioalkyl radical, a $C_1–C_6$ alkylthio radical, an amino radical or an amino radical protected with a $(C_1–C_6)$ alkylcarbonyl, carbamyl or $C_1–C_6$ alkylsulphonyl radical; one of the radicals $R_8$, $R_9$ and $R_{10}$ can also represent a second group Z which is identical to or different from the first group Z;

$R_{11}$ represents a $C_1–C_6$ alkyl radical; a $C_1–C_6$ monohydroxyalkyl radical; a $C_2–C_6$ polyhydroxyalkyl radical; an aryl radical; a benzyl radical; a $C_1–C_6$ aminoalkyl radical; a $C_1–C_6$ aminoalkyl radical in which the amine is protected with a $(C_1–C_6)$ alkylcarbonyl, carbamyl or $C_1–C_6$ alkylsulphonyl radical; a carboxy$(C_1–C_6)$alkyl radical; a cyano$(C_1–C_6)$alkyl radical; a carbamyl$(C_1–C_6)$alkyl radical; a $C_1–C_6$ trifluoroalkyl radical; a tri$(C_1–C_6)$alkylsilane$(C_1–C_6)$alkyl radical; a $C_1–C_6$ sulphonamidoalkyl radical; a $(C_1–C_6)$alkylcarboxy$(C_1–C_6)$alkyl radical; a $(C_1–C_6)$alkylsulphinyl ($C_1$–$C_6$)alkyl radical; a ($C_1$–$C_6$)alkylsulphonyl ($C_1$–$C_6$alkyl radical; a ($C_1$–$C_6$)alkylketo($C_1$–$C_6$) alkyl radical; an N-($C_1$–$C_6$)alkylcarbamyl($C_1$–$C_6$) alkyl radical; or an N-($C_1$–$C_6$)alkylsulphonamido ($C_1$–$C_6$)alkyl radical;

x and y are integers equal to 0 or 1, with the following conditions:

in the unsaturated cationic groups of formula (II):
when x=0, the linker arm D is attached to the nitrogen atom,
when x=1, the linker arm D is attached to one of the ring members E, G, J or L,
y can take the value 1 only when:
1) the ring members E, G, J and L simultaneously represent a carbon atom and the radical $R_7$ is borne by the nitrogen atom of the unsaturated ring; or
2) at least one of the ring members E, G, J and L represents a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M represents a divalent atom and when the radical $R_7$ is borne by the nitrogen atom of the unsaturated ring;

in the cationic groups of formula (IV):
when x=0, the linker arm is attached to the nitrogen atom bearing the radicals $R_8$ to $R_{10}$,
when x=1, two of the radicals $R_8$ to $R_{10}$ form, together with the nitrogen atom to which they are attached, a saturated 5- or 6-membered ring as defined above, and the linker arm D is borne by a carbon atom of the saturated ring;

$X^-$ represents a monovalent or divalent anion and is preferably chosen from a halogen atom such as chlorine, bromine, fluorine or iodine, a hydroxide, a hydrogen sulphate and a $C_1$–$C_6$ alkyl sulphate such as, for example, a methyl sulphate or an ethyl sulphate;

it being understood that:
the number of cationic groups Z of formula (II) or (III) is at least equal to 1; and
when one and only one of the radicals $R_4$ or $R_5$ or $R_6$ denotes a group Z in which the linker arm D represents an alkyl chain comprising a ketone function, then the ketone function is not directly linked to the nitrogen atom of the group $NR_4R_5$ when $R_1$, $R_2$, $R_3$, $R'_1$, $R'_2$, $R'_3$ or A represents $NR_4R_5$, or to the oxygen atom of the group $OR_6$ when $R_1$, $R_2$, $R_3$, $R'_1$, $R'_2$, $R'_3$ or A represents $OR_6$.

In formulae (I), (II), (III) and (IV) above, the alkyl and alkoxy radicals may be linear or branched.

The compounds of formula (I) can optionally be salified with strong inorganic acids such as HCl, HBr or $H_2SO_4$, or organic acids such as acetic acid, tartaric acid, lactic acid, citric acid or succinic acid.

Among the rings of the unsaturated groups Z of formula (II) above, mention may be made in particular, for example, of pyrrole, imidazole, pyrazole, oxazole, thiazole and triazole rings.

Among the rings of the unsaturated groups Z of formula (III) above, mention may be made in particular, for example, of pyridine, pyrimidine, pyrazine, oxazine and triazine rings.

Among the compounds of formula (I) above, mention may be made in particular of the following compounds:

bis(2-(3-methyl-3H-imidazol-1-ium)ethyl)(4-(4-nitrophenylazo)phenyl)amine dichloride monohydrate; and bis(2-(3-methyl-3H-imidazol-1-ium)ethyl)(4-(4-aminophenylazo)phenyl)amine dichloride.

The compounds of formula (I) according to the invention can be obtained easily, according to methods that are well known in the state of the art for obtaining quaternized amines, for example:

in one stage, by condensation of a phenyl-azo-benzene compound comprising a haloalkyl radical with a compound bearing a tertiary amine, or by condensing a phenyl-azo-benzene compound comprising a tertiary amine radical with a compound bearing a haloalkyl radical; or in two stages, by condensing a phenyl-azo-benzene compound comprising a haloalkyl radical with a compound bearing a secondary amine, or by condensing a halogenated phenyl-azo-benzene compound with an amino (disubstituted)alkylamine, followed by quaternization with an alkylating agent.

The quaternization step is generally, for convenience, the final step of the synthesis, but can be carried out earlier in the sequence of reactions leading to the preparation of the compounds of formula (I).

Another subject of the invention is a composition for dyeing keratin substances, containing, in a medium suitable for dyeing, an effective amount of at least one compound of formula (I) according to the invention.

Yet another subject of the invention is a composition for the direct dyeing of human keratin fibers such as the hair, containing, in a medium suitable for dyeing, an effective amount of at least one compound of formula (I) according to the invention.

The cationic phenyl-azo-benzene compound(s) of formula (I) according to the invention and/or the acid addition salt(s) thereof preferably represent from 0.005 to 12% by weight approximately, relative to the total weight of the dye composition, and even more preferably from 0.05 to 6% by weight approximately, relative to the total weight.

The compounds of formula (I) according to the invention can also be used in well-known oxidation-dyeing processes using oxidation dyes (oxidation-dye precursors and optionally couplers) to modify the shades obtained with the oxidation dyes or to enrich them with glints.

The dye composition according to the invention can also contain, in addition to the cationic phenyl-azo-benzene compounds of formula (I) according to the invention, other conventional direct dyes, in order to broaden the range of shades and to obtain a variety of tints, and in particular nitrobenzene dyes, such as nitrophenylenediamines, nitrodiphenylamines, nitroanilines, nitrophenyl ethers or nitrophenols, and nitropyridines, anthraquinone dyes, mono- or diazo dyes, triarylmethane dyes, azine dyes, acridine dyes, xanthene dyes, or metalliferous dyes.

The proportion of all these other additional direct dyes can range from 0.5 to 10% by weight approximately, relative to the total weight of the dye composition.

The medium which is suitable for dyeing (or the support) generally comprises water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol and propylene glycol monomethyl ether; aromatic alcohols such as benzyl alcohol or phenoxyethanol; and similar products and mixtures thereof.

The solvents can be present in proportions preferably ranging from 1 to 40% by weight approximately, relative to the total weight of the dye composition, and even more preferably from 5 to 30% by weight approximately.

Fatty amides such as mono- and diethanolamides of acids derived from coconut, of lauric acid or of oleic acid can also be added to the composition according to the invention, in concentrations ranging from about 0.05 to 10% by weight.

Surfactants that are well known in the state of the art, such as anionic, cationic, nonionic, amphoteric or zwitterionic surfactants or mixtures thereof, can also be added to the composition according to the invention, preferably in a proportion ranging from 0.1 to 50% by weight and advantageously from about 1 to 20% by weight relative to the total weight of the composition.

Thickeners can also be used, in a proportion ranging from about 0.2 to 5%.

The dye composition can also contain various common adjuvants such as antioxidants, fragrances, sequestering agents, dispersing agents, hair conditioners, preserving agents and opacifiers, as well as any other adjuvant commonly used in dyeing keratin substances.

Needless to say, a person skilled in the art will take care to select the optional additional compound(s) mentioned above, such that the advantageous properties intrinsically associated with the dye composition according to the invention are not, or are not substantially, adversely affected by the addition(s) envisaged.

The pH of the dye composition in accordance with the invention ranges generally from 3 to 12 approximately, and preferably from 5 to 11 approximately. It can be adjusted to the desired value using acidifying or basifying agents commonly used to dye keratin fibers.

Among the acidifying agents which can be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

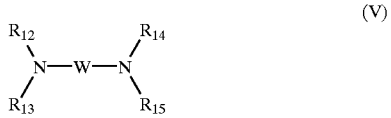

(V)

in which W is a propylene residue optionally substituted with a hydroxyl group or a $C_1$–$C_6$ alkyl radical; and $R_{12}$, $R_{13}$, $R_{14}$ and $R_{15}$, which may be identical or different, represent a hydrogen atom, a $C_1$–$C_6$ alkyl radical or a $C_1$–$C_6$ hydroxyalkyl radical.

The dye composition according to the invention can be in various forms, such as liquids, creams or gels, or in any other form which is suitable for dyeing keratin substances and especially human hair. In particular, it can be packaged under pressure in an aerosol can in the presence of a propellant and can form a mousse.

Another subject of the invention relates to a process for dyeing keratin fibers, and in particular human keratin fibers such as the hair, by direct dyeing, this process comprising allowing a composition containing at least one cationic phenyl-azo-benzene compound of formula (I) to act on wet or dry keratin fibers.

The composition according to the invention can be used as a leave-in composition, i.e., after the composition is applied to the fibers, they are dried without intermediate rinsing.

In other application methods, after allowing the composition to act on the fibers for an exposure time ranging from 3 to 60 minutes approximately, preferably from 5 to 45 minutes approximately, the fibers are rinsed, optionally washed and then rinsed again, and dried.

Concrete and non-limiting examples illustrating the invention will now be given.

PREPARATION EXAMPLE

Example 1

Bis(2-(3-Methyl-3H-imidazol-1-ium)ethyl)(4-(4-nitrophenylazo)phenyl)amine Dichloride Monohydrate

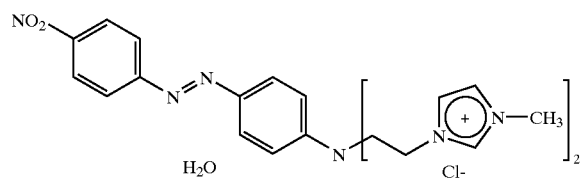

A mixture of 21.2 g (0.057 mol) of bis(2-chloroethyl)-(4-(4-nitrophenylazo)phenyl)amine (RN 66710-74-5) and 37.4 g (0.456 mol) of 1–methyl-1H-imidazole (RN 616-47-7) in 50 ml of toluene was refluxed for 8 hours.

The red solution became a suspension (crystalline precipitate).

40 ml of isobutanol and a further 37.4 g (0.456 mol) of 1-methyl-1H-imidazole were added. Refluxing was continued for 8 hours.

The crystalline precipitate was spin-dried, washed with toluene and purified by recrystallization from refluxing 96° ethanol.

26.8 g of red crystals of bis(2-(3-methyl-3H-imidazol-1-ium)ethyl)(4-(4-nitrophenylazo)phenyl)amine dichloride monohydrate, melting with decomposition at a temperature above 260° C. (Kofler), were obtained.

The elemental analysis for $C_{24}H_{28}N_8O_2Cl_2 \cdot H_2O$ was:

| % | C | H | N | O | Cl |
|---|---|---|---|---|---|
| theory | 52.46 | 5.50 | 20.39 | 8.74 | 12.90 |
| found | 52.60 | 5.47 | 20.50 | 8.55 | 13.10 |

EXAMPLES OF DYE COMPOSITIONS

Examples 1 and 2

The Two Direct Dye Compositions given in the Table below were Prepared (All Contents Expressed in Grams—A.M. Denotes Active Material)

|  | Example 1 | Example 2 |
|---|---|---|
| Dye of Example 1 | 0.549 |  |
| Dye of Example 1 |  | 0.549 |
| Hydroxyethylcellulose sold under the name | 0.77 | 0.77 |

-continued

|  | Example 1 | Example 2 |
|---|---|---|
| NATROSOL 250 MR by the company Aqualon | 5 | |
| Benzyl alcohol | 4 | 4 |
| Polyethylene glycol containing 300 ethylene oxide | 12 | 12 |
| ($C_8$–$C_{10}$)Alkyl polyglucoside as an aqueous solution containing 60% A.M., sold under the name ORAMIX CG 110 by the company SEPPIC | 6 A.M. | 6 A.M. |
| pH 7 phosphate buffer qs | 100 | |
| pH 9 phosphate buffer (boric acid/potassium chloride/sodium hydroxide) qs | | 100 |

Each of the above compositions was applied to locks of natural or permanent-waved grey hair comprising 90% white hairs, and was left to stand on the hair for 20 minutes. After rinsing with running water and drying, the hair was dyed in the shade given in the table below.

| Composition of Example 1 | Coppery |
|---|---|
| Composition of Example 2 | Coppery |

What is claimed is:

1. A dyeing composition for keratinous substances, comprising,
   (a) a medium suitable for dyeing keratinous substances; and
   (b) at least one compound of formula (I) below or an acid addition salt thereof, said at least one compound of formula (I) being present in said composition in an amount effective for direct dyeing of keratinous substances;

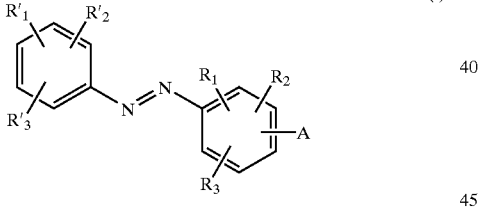

(I)

wherein:
$R_1$, $R_2$, $R_3$, $R'_1$, $R'_2$, and $R'_3$, which may be identical or different, are chosen from a hydrogen atom; a halogen atom; a group Z as defined below; a ($C_1$–$C_6$) alkyl-carbonyl radical; an amino($C_1$–$C_6$) alkylcarbonyl radical; an N-Z-amino($C_1$–$C_6$) alkylcarbonyl radical; an N-($C_1$–$C_6$)alkylamino ($C_1$–$C_6$)alkylcarbonyl radical; an N,N-di($C_1$–$C_6$) alkylamino($C_1$–$C_6$)alkylcarbonyl radical; an amino ($C_1$–$C_6$)alkylcarbonyl($C_1$–$C_6$)alkyl radical; an N-Z-amino($C_1$–$C_6$)alkylcarbonyl($C_1$–$C_6$)-alkyl radical; an N-($C_1$–$C_6$)alkylamino($C_1$–$C_6$)-alkylcarbonyl ($C_1$–$C_6$)alkyl radical; an N,N-di($C_1$–$C_6$)alkylamino ($C_1$–$C_6$)alkyl-carbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N-Z-amino-sulphonyl radical; a $C_1$–$C_6$ N-alkylaminosulphonyl radical; a $C_1$–$C_6$ N,N-dialkylaminosulphonyl radical; a $C_1$–$C_6$ aminosulphonylalkyl radical; a $C_1$–$C_6$ N-Z-aminosulphonylalkyl radical; an N-($C_1$–$C_6$) alkylaminosulphonyl($C_1$–$C_6$)alkyl radical; an N,N-di($C_1$–$C_6$)alkylaminosulphonyl($C_1$–$C_6$)alkyl radical; a carbamyl radical; an N-($C_1$–$C_6$)alkylcarbamyl radical; an N,N-di($C_1$–$C_6$)alkylcarbamyl radical; a carbamyl($C_1$–$C_6$)alkyl radical; an N-($C_1$–$C_6$) alkylcarbamyl($C_1$–$C_6$)alkyl radical; an N,N-di ($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy ($C_1$–$C_6$)alkyl radical; a $C_1$–$C_6$ trifluoroalkyl radical; a cyano radical; a nitro radical; an amino group $NR_4R_5$, wherein $R_4$ and $R_5$ are as defined below; a group $OR_6$ or $SR_6$, wherein $R_6$ is as defined below; and a $C_1$–$C_6$ aminoalkyl radical wherein the alkyl may be unsubstituted or substituted with one or more hydroxyl radicals and wherein the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, carbamyl, N-($C_1$–$C_6$) alkylcarbamyl or N,N-di($C_1$–$C_6$)-alkylcarbamyl, $C_1$–$C_6$ alkylsulphonyl, formyl, trifluoro($C_1$–$C_6$) alkylcarbonyl, ($C_1$–$C_6$)alkylcarboxyl and thiocarbamyl radicals, and from a group Z as defined below;

A is chosen from a group $NR_4R_5$, wherein $R_4$ and $R_5$ are as defined below, and a group $OR_6$, wherein $R_6$ is as defined below;

$R_4$ and $R_5$, which may be identical or different, are chosen from a hydrogen atom;

a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a cyano($C_1$–$C_6$) alkyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl ($C_2$–$C_6$)alkyl radical; a $C_1$–$C_6$ trifluoroalkyl radical; a $C_1$–$C_6$ sulphoalkyl radical; a ($C_1$–$C_6$) alkylcarboxyl($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; and a $C_1$–$C_6$ aminoalkyl radical wherein the alkyl can be unsubstituted or substituted with one or more hydroxyl radicals and wherein the amine is substituted with one or two identical or different radicals which are chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N-($C_1$–$C_6$) alkylcarbamyl or N,N-di($C_1$–$C_6$)alkylcarbamyl, $C_1$–$C_6$ alkylsulphonyl, formyl, trifluoro-($C_1$–$C_6$) alkylcarbonyl, ($C_1$–$C_6$)alkylcarboxyl, thiocarbamyl radicals, and a group Z as defined below, or which may together form, with the nitrogen atom to which they are attached, a carbonaceous 5- or 6-membered ring or a 5- or 6-membered ring comprising one or more identical or different hetero atoms;

$R_6$ is chosen from a hydrogen atom; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxyl($C_1$–$C_6$)alkyl radical; a cyano($C_1$–$C_6$)alkyl radical; a carbamyl($C_1$–$C_6$)

alkyl radical; an N-($C_1$–$C_6$)alkylcarbamyl($C_1$–$C_6$) alkyl radical; an N,N-di($C_1$–$C_6$)alkylcarbamyl ($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$) alkylaminosulphonyl($C_1$–$C_6$)alkyl radical; an N,N-di($C_1$–$C_6$)alkylaminosulphonyl($C_1$–$C_6$) alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; ($C_1$–$C_6$)alkylcarbonyl($C_1$–$C_6$)alkyl radical; a $C_1$–$C_6$ aminoalkyl radical, wherein the alkyl is unsubstituted or substituted with one or more hydroxyl radicals; a $C_1$–$C_6$ aminoalkyl radical wherein the alkyl is unsubstituted or substituted with one or more hydroxyl radicals and wherein the amine is substituted with one or two identical or different radicals which are chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, formyl, trifluoro($C_1$–$C_6$) alkylcarbonyl, ($C_1$–$C_6$)alkylcarboxyl, carbamyl, N-($C_1$–$C_6$)alkylcarbamyl, N,N-di($C_1$–$C_6$) alkylcarbamyl, thiocarbamyl, $C_1$–$C_6$ alkylsulphonyl radicals, and a group Z as defined below, or which may together form, with the nitrogen atom to which they are attached, a carbonaceous 5- or 6-membered ring or a 5- or 6-membered ring comprising one or more identical or different hetero atoms;

Z is chosen from the unsaturated cationic groups of formulae (II) and (III) below, and the saturated cationic groups of formula (IV) below:

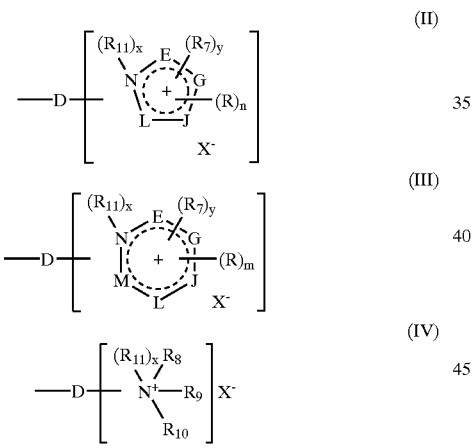

wherein:

D is a linker arm which is a linear or branched alkyl chain, which can be interrupted by one or more identical or different hetero atoms, can be substituted with one or more hydroxyl radicals or identical or different $C_1$–$C_6$ alkoxy radicals, and can bear one or more ketone functions;

the ring members E, G, J, L, and M, which may be identical or different, are chosen from carbon, oxygen, sulphur and nitrogen atoms;

n is an integer ranging from 0 to 4;

m is an integer ranging from 0 to 5;

the radicals R, which may be identical or different, are chosen from a second group Z which is identical to or different from the first group Z; a halogen atom; a hydroxyl radical; a $C_1$–$C_6$ alkyl radical; $C_1$–$C_6$ monohydroxyalkyl radical; a $C_2$–$C_6$ polyhydroxyalkyl radical; a nitro radical; a cyano radical; a cyano($C_1$–$C_6$)alkyl radical; a $C_1$–$C_6$ alkoxyl radical; a tri($C_1$–$C_6$)alkylsilane ($C_1$–$C_6$)alkyl radical; an amido radical; an aldehydo radical; a carboxyl radical; a ($C_1$–$C_6$) alkylcarbonyl radical; a thio radical; a $C_1$–$C_6$ thioalkyl radical; a $C_1$–$C_6$ alkylthio radical; an amino radical; an amino radical protected with a ($C_1$–$C_6$) alkylcarbonyl, carbamyl or $C_1$–$C_6$ alkylsulphonyl radical; and a group NHR" or NR"R, wherein R" and R, which may be identical or different, are chosen from a $C_1$–$C_6$ alkyl radical, a $C_1$–$C_6$ monohydroxyalkyl radical and a $C_2$–$C_6$ polyhydroxyalkyl radical;

$R_7$ is chosen from a $C_1$–$C_6$ alkyl radical; a $C_1$–$C_6$ monohydroxyalkyl radical; a $C_2$–$C_6$ polyhydroxyalkyl radical; a cyano($C_1$–$C_6$)alkyl radical; a tri ($C_1$–$C_6$)alkylsilane($C_1$–$C_6$)alkyl radical; a ($C_1$–$C_6$)alkoxy($C_1$–$C_6$)alkyl radical; a carbamyl-($C_1$–$C_6$)alkyl radical; a ($C_1$–$C_6$)alkylcarboxy ($C_1$–$C_6$)-alkyl radical; a benzyl radical; and a second group Z which is identical to or different from the first group Z;

$R_8$, $R_9$, and $R_{10}$, which may be identical or different, are chosen from a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a cyano($C_1$–$C_6$)alkyl radical; an aryl radical; a benzyl radical; a $C_1$–$C_6$ amidoalkyl radial; a tri($C_1$–$C_6$)alkylsilane($C_1$–$C_6$)alkyl radical; and a $C_1$–$C_6$ aminoalkyl radical wherein the amine is protected with a ($C_1$–$C_6$)alkylcarbonyl, carbamyl or $C_1$–$C_6$ alkylsulphonyl radical; or wherein two of the radicals $R_8$, $R_9$, and $R_{10}$ form, together with the nitrogen atom to which they are attached, a saturated carbonaceous 5- or 6-membered ring or a 5- or 6-membered ring comprising one or more identical or different hetero atoms; or further wherein one of the radicals $R_8$, $R_9$, and $R_{10}$ is a second group Z which is identical to or different from the first group Z;

$R_{11}$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical wherein the amine is protected with ($C_1$–$C_6$) alkylcarbonyl, carbamyl or $C_1$–$C_6$ alkylsulphonyl radical; a carboxy($C_1$–$C_6$)alkyl radical; a cyano($C_1$–$C_6$)alkyl radical; a carbamyl($C_1$–$C_6$) alkyl radical; a $C_1$–$C_6$ trifluoroalkyl radical; a tri($C_1$–$C_6$)alkylsilane($C_1$–$C_6$)alkyl radical; a $C_1$–$C_6$ sulphonamidoalkyl radical; a ($C_1$–$C_6$) alkylcarboxyl($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N-($C_1$–$C_6$) alkylcarbamyl($C_1$–$C_6$)alkyl radical; and an N-($C_1$–$C_6$)alkylsulphonamido($C_1$–$C_6$)alkyl radical;

x and y are integers equal to 0 or 1, with the provisos that:

in the unsaturated cationic groups of formula (II):

when x=0, the linker arm D is attached to the nitrogen atom, when x=1, the linker arm D is attached to one of the ring members E, G, J or L, y can take the value 1 only when:

1) the ring members E, G, J, and L are all carbon atoms, and the radical $R_7$ is borne by the nitrogen atom of the unsaturated ring; or 2) at least one of the ring members E, G, J, and L is a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L, or M,
y can take the value 1 only when at least one of the ring members E, G, J, L, and M is a divalent atom and when the radical $R_7$ is borne by the nitrogen atom of the unsaturated ring;

in the cationic groups of formula (IV):
when x=0, the linker arm is attached to the nitrogen atom bearing the radicals $R_8$, $R_9$, and $R_{10}$,
when x=1, two of the radicals $R_8$, $R_9$, and $R_{10}$ form, together with the nitrogen atom to which they are attached, a saturated carbonaceous 5- or 6-membered ring or a 5- or 6-membered ring comprising one or more identical or different hetero atoms, and the linker arm D is borne by a carbon atom of said saturated ring;

$X^-$ is a monovalent or divalent anion; with the provisos that:
in the compound of the formula (I), at least one of $R_1$, $R_2$, $R_3$, $R'_1$, $R'_2$, $R'_3$ and A comprise a cationic group Z of formula (II) or (III); and
when one and only one of the radicals $R_4$, $R_5$, or $R_6$ is a group Z wherein the linker arm D is an alkyl chain comprising a ketone function, then said ketone function is not directly attached to the nitrogen atom of the group $NR_4R_5$ or to the oxygen atom of the $OR_6$ group.

2. A composition according to claim 1, wherein said keratinous substances are human keratin fibers.

3. A composition according to claim 2, wherein said human keratin fibers are hair.

4. A composition according to claim 1, wherein said linker arm D is a linear or branched alkyl chain comprising from 1 to 14 carbon atoms.

5. A composition according to claim 1, wherein said linker arm D is a linear or branched alkyl chain, which is interrupted by one or more identical or different hetero atoms chosen from oxygen, sulphur and nitrogen atoms.

6. A composition according to claim 1, wherein the rings of the unsaturated groups Z of formula (II) are chosen from pyrrole, imidazole, pyrazole, oxazole, thiazole and triazole rings.

7. A composition according to claim 1, wherein the rings of the unsaturated groups Z of formula (III) are chosen from pyridine, pyrimidine, pyrazine, oxazine and triazine rings.

8. A composition according to claim 1, wherein two of the radicals $R_8$, $R_9$ and $R_{10}$ in formula (IV) together form, with the nitrogen atom to which they are attached, a pyrrolidine ring, a piperidine ring, a piperazine ring or a morpholine ring, wherein said ring is unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$) alkyl radical, a $C_1$–$C_6$ alkoxy radical, a tri($C_1$–$C_6$) alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical.

9. A composition according to claim 1, wherein $X^-$ is chosen from a halogen atom, a hydroxide, a hydrogen sulphate and a $C_1$–$C_6$ alkyl sulphate.

10. A composition according to claim 1, wherein said at least one compound of formula (I) is chosen from:
bis(2-(3-methyl-3H-imidazol-1-ium)ethyl)(4-(4-nitrophenylazo)phenyl)amine dichloride monohydrate; and
bis(2-(3-methyl-3H-imidazol-1-ium)ethyl)(4-(4-aminophenylazo)phenyl)amine dichloride.

11. A composition according to claim 1, wherein said acid addition salts are chosen from hydrochlorides, hydrobromides, sulphates, citrates, succinates, tartrates, lactates and acetates.

12. A composition according to claim 1, wherein said composition has a pH ranging from 3 to 12.

13. A composition according to claim 1, wherein said at least one compound of formula (I) is present in an amount ranging from 0.005 to 12% by weight relative to the total weight of the composition.

14. A composition according to claim 13, wherein said at least one compound of formula (I) is present in an amount ranging from 0.05 to 6% by weight relative to the total weight of the composition.

15. A composition according to claim 1, wherein said medium suitable for dyeing is an aqueous medium comprising water and/or organic solvents, said medium being present in said composition in an amount ranging from 1 to 40% by weight relative to the total weight of the composition.

16. A process for dyeing keratinous fibers by direct dyeing, comprising applying a dyeing composition to wet or dry keratinous fibers, said dyeing composition comprising, in a medium suitable for dyeing, at least one compound of formula (I) below or an acid addition salt thereof, said at least one compound of formula (I) being present in said composition in an amount effective for direct dyeing of keratinous fibers:

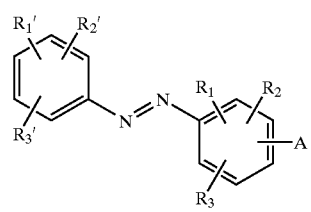

(I)

wherein:
$R_1$, $R_2$, $R_3$, $R'_1$, $R'_2$, $R'_3$, which may be identical or different, are chosen from a hydrogen atom; a halogen atom; a group Z as defined below; a ($C_1$–$C_6$)alkylcarbonyl radical; an amino($C_1$–$C_6$)alkylcarbonyl radical; an N-Z amino($C_1$–$C_6$)alkylcarbonyl radical; an N-($C_1$–$C_6$)alkylamino($C_1$–$C_6$)alkylcarbonyl radical; an N,N-di($C_1$–$C_6$)alkylamino($C_1$–$C_6$)alkylcarbonyl radical; an amino($C_1$–$C_6$)alkylcarbonyl ($C_1$–$C_6$) alkyl radical; an N-Z-amino($C_1$–$C_6$)alkylcarbonyl($C_1$–$C_6$)-alkyl radical; an N-($C_1$–$C_6$)alkylamino($C_1$–$C_6$)-alkylcarbonyl($C_1$–$C_6$)alkyl radical; an N,N-di($C_1$–$C_6$) alkylamino($C_1$–$C_6$)alkyl-carbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N-Z-aminosulphonyl radical; a $C_1$–$C_6$ N-alkylaminosulphonyl radical; a $C_1$–$C_6$ N,N-dialkylaminosulphonyl radical; a $C_1$–$C_6$ aminosulphonylalkyl radical; a $C_1$–$C_6$ N-Z-aminosulphonylalkyl radical; an N-($C_1$–$C_6$)alkylaminosulphonyl($C_1$–$C_6$) alkyl radical; an N,N-di($C_1$–$C_6$)alkylaminosulphonyl ($C_1$–$C_6$)alkyl radical; a carbamyl radical; an N-($C_1$–$C_6$) alkylcarbamyl radical; an N,N-di($C_1$–$C_6$) alkylcarbamyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ trifluoroalkyl radical; a cyano radical; a nitro radical; an amino group $NR_4R_5$, wherein $R_4$ and $R_5$ are as defined below; a group $OR_6$ or $SR_6$, wherein $R_6$ is as defined below; and a $C_1$–$C_6$ aminoalkyl radical wherein the alkyl may be unsubstituted or substituted with one or more hydroxyl radicals and wherein the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N-($C_1$–$C_6$)alkylcarbamyl or N,N-di($C_1$–$C_6$)-alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, and from a group Z as defined below;

A is chosen from a group $NR4R_5$, wherein $R_4$ and $R_5$ are as defined below, and a group $OR_6$, wherein $R_6$ is as defined below;

$R_4$ and $R_5$, which may be identical or different, are chosen from a hydrogen atom; a group Z as defined below; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; an aryl radical; a benzyl radical; a cyano($C_1$–$C_6$)alkyl radical; a carbamyl ($C_1$–$C_6$)alkyl radical; an N-($C_1$–$C_6$)alkylcarbamyl ($C_1$–$C_6$)alkyl radical; an N,N-di($C_1$–$C_6$)alkylcarbamyl ($C_1$–$C_6$)alkyl radical; a thiocarbamyl ($C_2$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N-Z-aminosulphonylalkyl radical; an N-($C_1$–$C_6$) alkylaminosulphonyl ($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; and a $C_1$–$C_6$ aminoalkyl radical wherein the alkyl can be unsubstituted or substituted with one or more hydroxyl radicals and wherein the amine is substituted with one or two identical or different radicals which are chosen from $C_1$–$C_6$ alkyl, $C_1$–$C_6$ monohydroxyalkyl, ($C_2$–$C_6$)polyhydroxyalkyl; ($C_1$–$C_6$)alkylcarbonyl, carbamyl, N-($C_1$–$C_6$) alkylcarbamyl or N,N-di($C_1$–$C_6$)alkylcarbamyl, $C_1$–$C_6$ alkylsulphonyl, formyl, trifluoro-($C_1$–$C_6$) alkylcarbonyl, ($C_1$–$C_6$)alkylcarboxyl, thiocarbamyl radicals, and a group Z as defined below, or which may together form, with the nitrogen atom to which they are attached, a carbonaceous 5- or 6-membered ring or a 5- or 6-membered ring comprising one or more identical or different hetero atoms;

$R_6$ is chosen from a hydrogen atom; a $C_1$–$C_6$ alkyl radical; a $C_1$–$C_6$ monohydroxyalkyl radical; a $C_2$–$C_6$ polyhydroxyalkyl radical; a group Z as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxyl($C_1$–$C_6$)alkyl radical; a cyano ($C_1$–$C_6$)alkyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-($C_1$–$C_6$)alkylaminosulphonyl($C_1$–$C_6$)alkyl radical; an N,N-di($C_1$–$C_6$)alkylaminosulphonyl ($C_1$–$C_6$)alkyl radical; a ($C_1$–$C_6$)alkylsulphinyl($C_1$–$C_6$) alkyl radial; a ($C_1$–$C_6$)alkylsulphonyl($C_1$–$C_6$)alkyl radical; a ($C_1$–$C_6$)alkylcarbonyl($C_1$–$C_6$)alkyl radical; a $C_1$–$C_6$ aminoalkyl radical, wherein the alkyl is unsubstituted or substituted with one or more hydroxyl radicals; a $C_1$–$C_6$ aminoalkyl radical wherein the alkyl is unsubstituted or substituted with one or more hydroxyl radicals and wherein the amine is substituted with one or two identical or different radicals which are chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, formyl, trifluoro($C_1$–$C_6$)alkylcarbonyl, ($C_1$–$C_6$) alkylcarboxyl, carbamyl, N-($C_1$–$C_6$)alkylcarbamyl, N,N-di($C_1$–$C_6$)alkylcarbamyl, thiocarbamyl, $C_1$–$C_6$ alkylsulphonyl radicals, and a group Z as defined below, or which may together form, with the nitrogen atom to which they are attached, a carbonaceous 5- or 6-membered ring or a 5- or 6-membered ring comprising one or more identical or different hetero atoms;

Z is chosen from the unsaturated cationic groups of formulae (II) and (III) below, and the saturated cationic groups of formula (IV) below:

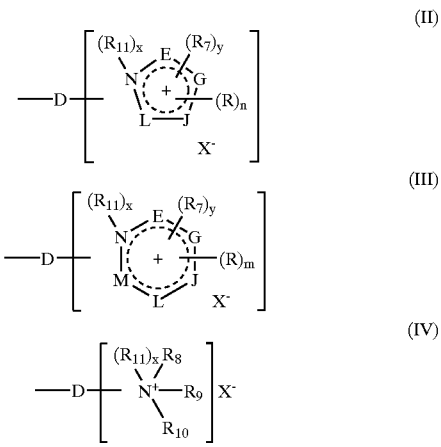

wherein:
D is a linker arm which is a linear or branched alkyl chain, which can be interrupted by one or more identical or different hetero atoms, can be substituted with one or more hydroxyl radicals or identical or different $C_1$–$C_6$ alkoxy radicals, and can bear one or more ketone functions;

the ring members E, G, J, L, and M, which may be identical or different, are chosen from carbon, oxygen, sulphur and nitrogen atoms;

n is an integer ranging from 0 to 4;

m is an integer ranging from 0 to 5;

the radicals R, which may be identical or different, are chosen from a second group Z which is identical to or different from the first group Z; a halogen atom; a hydroxyl radical; a $C_1$–$C_6$ alkyl radical; a $C_1$–$C_6$ monohydroxyalkyl radical; a $C_2$–$C_6$ polyhydroxyalkyl radical; a nitro radical; a cyano radical; a cyano($C_1$–$C_6$) alkyl radical; a $C_1$–$C_6$ alkoxy radical; a tri($C_1$–$C_6$) alkylsilane($C_1$–$C_6$)alkyl radical; an amido radical, an aldehydo radical; a carboxyl radical; a ($C_1$–$C_6$) alkylcarbonyl radical; a thio radical; a $C_1$–$C_6$ thioalkyl radical; a $C_1$–$C_6$ alkylthio radical; an amino radical; an amino radical protected with a ($C_1$–$C_6$)alkylcarbonyl, carbamyl or $C_1$–$C_6$ alkylsulphonyl radical; and a group NHR" or NR"R, wherein R" and R, which may be identical or different, are chosen from a $C_1$–$C_6$ alkyl radical, a $C_1$–$C_6$ monohydroxyalkyl radical and a $C_2$–$C_6$ polyhydroxyalkyl radical;

$R_7$ is chosen from a $C_1$–$C_6$ alkyl radical; a $C_1$–$C_6$ monohydroxyalkyl radical; a $C_2$–$C_6$ polyhydroxyalkyl radical; a cyano($C_1$–$C_6$)alkyl radical; a tri($C_1$–$C_6$)alkylsilane($C_1$–$C_6$)alkyl radical; a ($C_1$–$C_6$)alkoxy($C_1$–$C_6$)alkyl radical; a carbamyl-($C_1$–$C_6$)alkyl radical; a ($C_1$–$C_6$)alkylcarboxy($C_1$–$C_6$)-alkyl radical; a benzyl radical; and a second group Z which is identical to or different from the first group Z;

$R_8$, $R_9$, and $R_{10}$, which may be identical or different, are chosen from a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a cyano($C_1$–$C_6$)alkyl radical; an aryl radical; a benzyl radical; a ($C_1$–$C_6$)amidoalkyl radical; a tri($C_1$–$C_6$)alkylsilane($C_1$–$C_6$)alkyl radical; and a ($C_1$–$C_6$) aminoalkyl radical wherein the amine is protected with a ($C_1$–$C_6$)alkylcarbonyl, carbamyl or $C_1$–$C_6$ alkylsulphonyl radical; or wherein two of the radicals $R_8$, $R_9$, and $R_{10}$ form, together with the nitrogen atom to which they are attached, a saturated carbonaceous 5- or 6-membered ring or a 5- or 6-membered ring comprising one or more identical or different hetero atoms; or further wherein one of the radicals $R_8$, $R_9$, and $R_{101}$ is a second group Z which is identical to or different from the first group Z;

$R_{11}$ is chosen from a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical; a $C_1$–$C_6$ aminoalkyl radical wherein the amine is protected with a ($C_1$–$C_6$) alkylcarbonyl, carbamyl or $C_1$–$C_6$ alkylsulphonyl radical; a carboxy($C_1$–$C_6$)alkyl radical; a cyano($C_1$–$C_6$)alkyl radical; a carbamyl ($C_1$–$C_6$) alkyl radical; a $C_1$–$C_6$ trifluoroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy($C_1$–$C_6$)alkyl radical; a ($C_1$–$C_6$)alkylsulphinyl ($C_1$–$C_6$)alkyl radical; a ($C_1$–$C_6$)alkylsulphonyl ($C_1$–$C_6$)alkyl radical; a ($C_1$–$C_6$)alkylketo($C_1$–$C_6$) alkyl radical; an N-($C_1$–$C_6$)alkylcarbamyl($C_1$–$C_6$) alkyl radical; and an N-($C_1$–$C_6$)alkylsulphonamido ($C_1$–$C_6$)alkyl radical;

x and y are integers equal to 0 or 1, with the provisos that:

in the unsaturated cationic groups of formula (II):
when x=0, the linker arm D is attached to the nitrogen atom,
when x=1, the linker arm D is attached to one of the ring members E, G, J or L,
y can take the value 1 only when:
1) the ring members E, G, J, and L are all carbon atoms, and the radical $R_7$ is borne by the nitrogen atom of the unsaturated ring; or
2) at least one of the ring members E, G, J, and L is a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L, or M,
y can take the value 1 only when at least one of the ring members E, G, J, L, and M is a divalent atom and when the radical $R_7$ is borne by the nitrogen atom of the unsaturated ring;

in the cationic groups of formula (IV):
when x=0, the linker arm is attached to the nitrogen atom bearing the radicals $R_8$, $R_9$, and $R_{10}$,
when x=1, two of the radicals $R_8$, $R_9$, and $R_{10}$ form, together with the nitrogen atom to which they are attached, a saturated carbonaceous 5- or 6-membered ring or a 5- or 6-membered ring comprising one or more identical or different hetero atoms, and the linker arm D is borne by a carbon atom of said saturated ring;

X is a monovalent or divalent anion;
with the provisos that:
in the compound of the formula (I), at least one of $R_1$, $R_2$, $R_3$, $R'_1$, $R'_2$, $R'_3$ and A comprise a cationic group Z of formula (II) or (III); and when one and only one of the radicals $R_4$, $R_5$, or $R_6$ is a group Z wherein the linker arm D is an alkyl chain comprising a ketone function, then said ketone function is not directly attached to the nitrogen atom of the group $NR_4R_5$ or to the oxygen atom of the $OR_6$ group.

17. A process according to claim 16, wherein said keratinous fibers are human keratin fibers.

18. A process according to claim 17, wherein said human keratin fibers are hair.

19. A process according to claim 16, wherein said dyeing composition is applied to dry or wet keratinous fibers, and said fibers are dried without intermediate rinsing.

20. A process according to claim 16, wherein said dyeing composition is applied to dry or wet keratinous fibers, and after said composition is optionally allowed to act on said fibers for an exposure time ranging from 3 to 60 minutes, said fibers are rinsed, optionally washed and rinsed again, and dried.

* * * * *

UNITED STATES PATENT AND TRADEMARK OFFICE
CERTIFICATE OF CORRECTION

PATENT NO. : 6,458,167 B1
APPLICATION NO. : 09/484998
DATED : October 1, 2002
INVENTOR(S) : Alain Genet and Alain Lagrange It is certified that error appears in the above-identified patent and that said Letters Patent is hereby corrected as shown below:

Title page, item (75), Inventors, "Alan Lagrange" should read --Alain Lagrange--.

Column 11, line 10, before "$(C_1-C_6)$alkylcarbonyl$(C_1-C_6)$alkyl" insert --a--.

Column 13, line 22, after "$X^-$" insert a space.

Column 14, in formula (I), lines 37-45, " 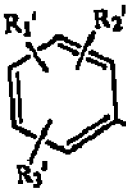 " should read -- 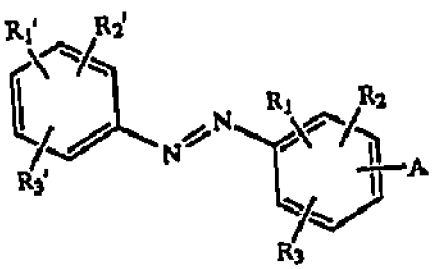 --.

Column 15, line 23, "NR4R$_5$" should read --$NR_4R_5$--.

Column 17, line 31, "$R_{101}$" should read --$R_{10}$--.

Signed and Sealed this

First Day of May, 2007

JON W. DUDAS
*Director of the United States Patent and Trademark Office*